United States Patent [19]

Jendersee et al.

[11] Patent Number: 5,836,965
[45] Date of Patent: Nov. 17, 1998

[54] STENT DELIVERY AND DEPLOYMENT METHOD

[76] Inventors: Brad Jendersee; Robert Lashinski, both of 5345 Skylane Blvd., Santa Rosa, Calif. 95403

[21] Appl. No.: 478,192

[22] Filed: Jun. 7, 1995

Related U.S. Application Data

[63] Continuation-in-part of Ser. No. 326,023, Oct. 19, 1994, abandoned.

[51] Int. Cl.⁶ .................................................. A61M 29/00
[52] U.S. Cl. .............................. 606/198; 606/194; 623/1; 623/12; 604/96
[58] Field of Search ................................ 606/1, 108, 191, 606/194, 195, 198, 200; 604/96–104; 623/1, 12

[56] References Cited

U.S. PATENT DOCUMENTS

| | | |
|---|---|---|
| 5,108,416 | 4/1992 | Ryan et al. . |
| 5,158,548 | 10/1992 | Lau et al. . |
| 5,242,399 | 9/1993 | Lau et al. . |
| 5,445,646 | 8/1995 | Euteneuer et al. ...................... 606/198 |
| 5,571,135 | 11/1996 | Fraser et al. ............................... 604/96 |

*Primary Examiner*—Michael Buiz
*Assistant Examiner*—William Lewis
*Attorney, Agent, or Firm*—Richard L. Klein

[57] ABSTRACT

A encapsulated stent device for implantation within the vascular system includes a balloon of a balloon catheter formed around and adhered to a wire-like stent so that the outer surface of the device is more regular for delivery through the vascular system without an exterior sheath. The encapsulation securely anchors the stent to the balloon and maintains a low profile for negotiation of tortuous and narrowed vessels. Encapsulation requires placement of the stent over the balloon, placement of a sheath over the stent on the balloon, heating and preferably pressurization of the balloon to cause it to expand around the stent within the sheath, and cooling while preferably maintaining pressure to cause the balloon to adhere to the stent and to set the shape of the expanded balloon. Retainers may be placed at the distal and/or proximal ends of the stent during the encapsulation process, or the balloon material may expand to form retainers. The balloon defines at least three folded wings for symmetrical expansion of the stent, and one or more connected or non-connected stents may be encapsulated depending upon the area to be treated.

14 Claims, 5 Drawing Sheets

STENT DELIVERY AND DEPLOYMENT METHOD

This application is a continuation-in-part of U.S. patent application Ser. No. 08/326,023, filed on Oct. 19, 1994 abandoned.

FIELD OF THE INVENTION

This invention relates to medical implant devices. More specifically, the invention relates to a stent encapsulated by an expandable balloon for delivery and deployment in narrowing coronary or peripheral vessels in humans.

DESCRIPTION OF THE PRIOR ART

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

An important development for treating atherosclerosis and other forms of coronary narrowing is percutaneous transluminal coronary angioplasty, hereinafter referred to as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

Angioplasty is typically performed as follows: A thin walled hollow guiding catheter is introduced into the body via a relatively large vessel, such as the femoral artery in the groin area or the brachial artery in the arm. Once access to the femoral artery is achieved, a short hollow sheath, or guiding catheter, is inserted to maintain a passageway during the procedure. The flexible guiding catheter must negotiate an approximately 180 degree turn through the aortic arch to descend into the aortic cusp where entry may be gained to either the left or the right coronary artery, as desired.

After the guiding catheter is advanced to the area to be treated by angioplasty, a flexible guidewire is inserted into the guiding catheter through an expandable balloon (described infra) and advanced to the area to be treated. The guidewire is advanced across the lesion, or "wires" the lesion, in preparation for the advancement of a balloon catheter having an expandable balloon portion composed of polyethylene, polyvinyl chloride, polyolefin, or other suitable substance, across the guide wire. Currently, most balloons utilize two folded wings wrapped around the hollow catheter tube. The balloon catheter is placed into position by sliding it along the guide wire. The use of the relatively rigid guide wire is necessary for steerability to advance the catheter through the narrowed lumen of the artery and to direct the balloon, which is typically quite flexible, across the lesion. Radiopaque markers in the balloon segment of the catheter facilitate positioning across the lesion. The balloon catheter is then inflated with contrast material to permit fluoroscopic viewing during treatment. The balloon is alternately inflated and deflated until the lumen of the artery is satisfactorily enlarged.

Unfortunately, while the affected artery generally can be enlarged, in some instances the vessel restenoses chronically, or closes down acutely, negating the positive effect of the angioplasty procedure. In the past, such restenosis has frequently necessitated repeat PTCA or open heart surgery. While such restenosis does not occur in the majority of cases, it occurs frequently enough that such complications comprise a significant percentage of the overall failures of the PTCA procedure, for example, twenty-five to thirty-five percent of such failures.

To lessen the risk of restenosis, various devices have been proposed for mechanically keeping the affected vessel open after completion of the angioplasty procedure. Such mechanical endoprosthetic devices, which are generally referred to as stents, are typically inserted into the vessel, positioned across the lesion, and then expanded to keep the passageway clear. Effectively, the stent overcomes the natural tendency of the vessel walls of some patients to close back down, thereby maintaining a more normal flow of blood through that vessel than would be possible if the stent were not in place.

Various types of stents have been proposed, including self-expandable and expandable stents, although to date none has proven completely satisfactory. Expandable stents generally are conveyed to the area to be treated on balloon catheters or other expandable devices. For insertion, the stent is positioned in a compressed configuration along the delivery device, such as a balloon catheter defining a balloon with two folded and wrapped wings, to make the stent diameter as small as possible. After the stent is positioned across the lesion, it is expanded by the delivery device, causing the length of the stent to contract and the diameter to expand. Depending on the materials used in construction of the stent, the stent maintains the new shape either through mechanical force or otherwise.

One such expandable stent for delivery on a balloon catheter is the Palmaz stent (U.S. Pat. No. 4,733,665) which may be thought of as a stainless steel cylinder having a number of slits in its circumference, resulting in a mesh when expanded. The stainless steel cylinder is compressed onto the outside of a non-expanded balloon catheter which includes stent retainer rings at each end of the stent to help to maintain the stent on the balloon. Also, it is advisable to place a sheath over the compressed stent and balloon assembly to retain the stent on the balloon and to create an even outer surface on the assembly for negotiation through the narrowed vessels. Boneau U.S. Pat. No. 5,292,331 provides a unitary wire-like stent structure configured to form a plurality of upper and lower axial peaks, and is delivered and expanded in a similar manner.

Significant difficulties have been encountered with deployment of known prior art stents, including difficulty in maintaining the stent on the balloon and in achieving symmetrical expansion of the stent when deployed. Currently, some stent delivery systems retain the stent on the delivery catheter by means of either (a) plastically deforming the stent so that it is crimped onto the balloon, or (b) having the stent exhibit a small enough internal diameter to act as an interference fit with the outside diameter of the balloon catheter. The disadvantage with these methods is that the limited amount of securement between the stent and the balloon is not always adequate to insure that the stent will properly stay in place while advancing the stent to and through the target lesion. Additionally, the outer surface of the delivery device is uneven because the stent generally extends outwardly beyond the balloon and may contact a narrowed vessel wall and be displaced while the catheter negotiates a narrowed vessel. Most known expandable stent delivery systems utilize a removable sheath system on the outside of the stent, with or without retainer rings, that is removed once the stent is at the delivery site. This method protects the stent and provides a smooth surface for easier passage through vessels, but the method increases the crossing profile of the delivery device thereby decreasing the device's ability to track through narrowed and tortuous vasculature. This and other complications have resulted in a low level of acceptance for such stents within the medical community, and to date stents have not been accepted as a practical method for treating chronic restenosis.

A long felt need exists for a delivery and deployment method for stents which ensures positional stability of the stent during delivery without the need for an external sheath, thereby substantially decreasing the cross sectional profile of the balloon delivery device, and ensures symmetrical expansion of the stent at deployment.

SUMMARY OF THE INVENTION WITH OBJECTS

The stent delivery and deployment method of this invention provides a frozen-in balloon in intimate contact with, and/or surrounding, a stent to assure stent attachment to the balloon, i.e. excapsulation. This method is especially valuable at the proximal and distal ends of the stent for delivery purposes because a smoother transition occurs between the distal and proximal surfaces of the balloon catheter and the distal and proximal ends of the stent, and it also is effective along substantially the entire length of the stent. The frozen-in balloon form is achieved by encapsulating the stent so that the balloon may expand part way around the stent and adhere thereto. The preferred method of encapsulating the stent and balloon includes the steps of compressing the stent on the outside of the balloon, placing a sheath over the compressed stent to prevent expansion, and exposing the sheathed stent and balloon to an elevated temperature while pressurizing the balloon. The elevated temperature and pressurization causes the balloon to expand from below the stent to fill at least some of the spaces between the stent and the sheath. Following expansion and exposure to an elevated temperature, the balloon and stent are cooled while maintaining pressure in the balloon, so that the balloon profile will be "frozen around" (formed and somewhat adhered to) the stent. Alternatively, heat without pressurization of the balloon may be sufficient for encapsulation when the compressive forces of the sheath against the stent, which is pressed against the heated balloon, enables encapsulation of the stent.

If desired, the encapsulated stent may include conventional retainers at the proximal and/or distal end of the balloon. Such retainers may be located on top of the balloon or within the balloon. Additionally, the balloon itself may be used to form one or more stent retainers during encapsulation. In this aspect of the invention, a space is defined between the balloon and the sheath, proximal and/or distal to the stent, so that the balloon expands to occupy the space and form one or more retainers during the encapsulation process. Retainers assist in delivery by providing a smooth transition between the encapsulated stent and the catheter surface.

The preferred balloon for the method described above defines multiple (three or more) folded and wrapped "wings" or radial extensions on a balloon delivery device to assure radially symmetrical stent expansion during deployment. The preferred balloon utilizes four wings for a Boneau stent having four axial turns at each end, and the balloon length and number of wings may be tailored to the particular stent or stents to be deployed. By utilizing more than two wings, more symmetrical stent deployment and vessel coverage can be achieved. Symmetrical stent deployment results in symmetrical expansion and support of the target lesion thereby suggesting use of multiple folds for standard PTCA balloon catheters with or without stents.

The method of this invention may be used with most self-expanding and expandable prior art stents, such as tubular slotted stents, and including connected stents, articulated stents, and multiple connected or non-connected stents. It is preferred to use a stent apparatus such as the Boneau stent which is formed preferably from a single piece of wire defining axial bends or turns between straight segments. The stent apparatus can then be encapsulated on a balloon catheter using the inventive method, delivered to the affected vessel and expanded in place, all as described herein. Some of the intended uses include PTCA type stenting, PTA type stenting, graft support, graft delivery, INR use, GI tract use, drug delivery, and biliary stenting.

A general object of the present invention is to provide a stent delivery and deployment method that overcomes the drawbacks and limitations of the prior art.

A specific object of the present invention is to provide a stent delivery and deployment method that eliminates the need for a deployment sheath and results in a low profile device with a more regular outer surface that may be delivered through tortuous, narrowed vessel.

Another specific object of the present invention is to provide a stent delivery and deployment method which encapsulates the balloon and stent thereby securing the stent to the balloon and decreasing the profile of the stent and balloon.

Yet another specific object of the present invention is to provide a stent delivery and deployment method which includes a balloon with three or more wrapped and folded wings to ensure symmetrical deployment of the stent and expansion of the lesion to be treated.

One more specific object of the present invention is to provide an encapsulated stent and balloon have a retainer at the distal and/or proximal ends of the stent for maintaining the stent on the balloon and for forming a smooth outer surface on the encapsulated stent device.

Still another specific object of the invention is to provide a method for encapsulating the majority of expandable and self-expanding stents for treating vessels in humans.

These and other objects, advantages and features of the present invention will become more apparent upon considering the following detailed description of preferred embodiments, presented in conjunction with the accompanying drawings.

DETAILED DESCRIPTION OF PREFERRED EMBODIMENTS

Figure 1:
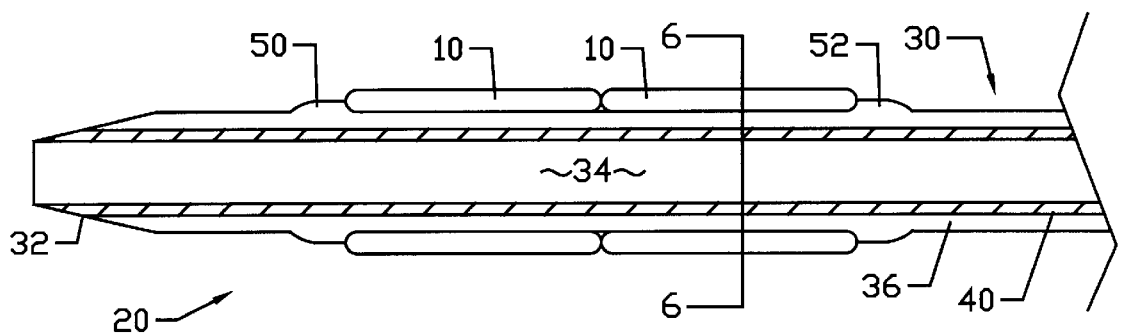
FIG. 1 is a longitudinal cross sectional view of two encapsulated stents and a balloon embodying the principles of the present invention and shown on a balloon catheter device.

FIG. 1 shows an encapsulated stent assembly 20 embodying the principles of the present invention. Two stent segments 10 are shown, and it will be recognized by those skilled in the art that one or more stent segments 10 may be used depending upon the size and configuration of the narrowed vessel to be treated. Additionally, when more than one stent segment 10 is used, the segments may be connected together by articulated or rigid joints, or multiple single stent segments may be deployed on the balloon catheter 30.

Figure 4:
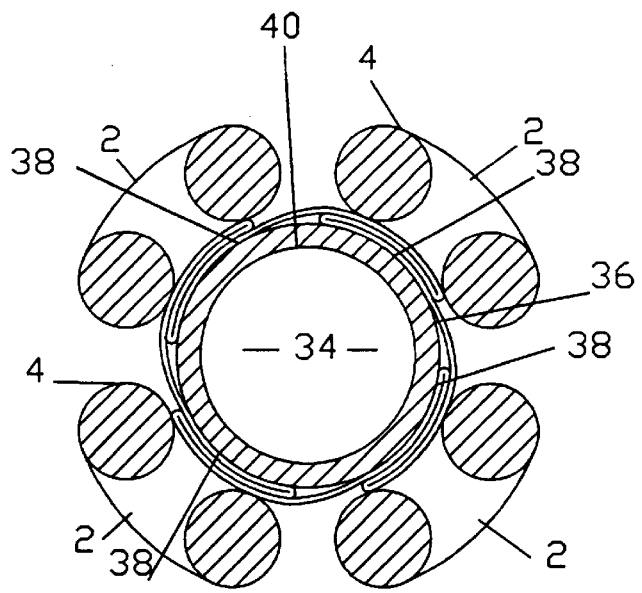
FIG. 4 is a cross sectional view taken along lines 4—4 of FIG. 2 and showing four folded and wrapped wings of the balloon beneath one of the stents.

The balloon catheter 30 preferably is of a low profile design defining a tapered distal tip 32, and an inner lumen 34 for insertion of a conventional guide wire (not shown). Any conventional or modified balloon catheter device may be used, such as a PTCA balloon catheter, and it is preferred that the expandable balloon portion 36 be configured on the catheter 30 so that the collapsed balloon defines three or more folded wings 38 which are wrapped around the outside of the catheter tube 40 as best shown in FIG. 4. In the embodiment in FIG. 4, the balloon 36 defines four folds 38 wrapped around the catheter tube 40 in a clockwise direction.

The preferred balloon 36 is formed from a material such as polyethylene, polyethylene terephthalate (PET), or from nylon or the like. The length and diameter of the balloon may be selected to accommodate the particular configuration of the stent to be encapsulated. The balloon may be carried on any catheter, although PTCA low profile catheters and over the wire catheters are preferred. The wings of the balloon are formed by pulling the balloon catheter through a forming tool having a generally cylindrical cross section and defining a terminal opening configured to produce the desired number of wings in the balloon. For instance, configuration of the terminal opening may include three or four slits radiating outwardly from the end of the forming tool, depending upon the number of folds to be produced. As the balloon catheter is pulled through the forming tool, the balloon is pushed through the configured terminal opening and exits having, for instance, three separate flutes. The balloon catheter bearing the fluted balloon portion then is pulled into a sheath, preferably a two part sheath made of Teflon or other suitable materials, so that the flutes fold and wrap around the catheter in a clockwise direction to form a generally spiral configuration around the catheter. The sheath-balloon catheter assembly is subjected to heat, preferably by placing the assembly in a heat set oven, to form a crease in substantially the length of each of the folded flutes. The sheath also may be of unitary construction. Following heat setting, the balloon 36 retains the creases formed in the wings and defines a generally symmetrical, cylindrical cross section, as best seen in FIG. 4.

Referring now to FIGS. 1–5, the Boneau stent is shown for illustration purposes only, and Boneau U.S. Pat. No. 5,292,331 is hereby incorporated by reference. Each of the stent segments 10 is preferably a short, single wire stent 10 having an expandable, generally cylindrical body portion defining an inside surface and an outside surface. In the stent segments 10 shown, the single piece of wire is bent to form a plurality of upper and lower axial turns 2. The plurality of upper turns 2 are connected to the plurality of lower turns 2 by substantially straight sections 4. The axial turns 2 can be seen to permit the stent segment 10 to be compressed or expanded over a wide range while still maintaining a significant mechanical force, such as required to prevent a vessel from restenosis or recoiling.

The stent segments 10 are preferably constructed of implantable materials having good mechanical strength, such as implantable quality stainless steel wire. The outside of the stent segments may be selectively plated with platinum, or other implantable radiopaque substances, to provide improved visibility during fluoroscopy. The cross-sectional shape of the finished stent segment 10 may be circular, ellipsoidal, rectangular, hexagonal, square, or other polygon, although at present it is believed that circular or ellipsoidal may be preferable.

The minimum length of each stent segment 10, or the distance between the upper turns and lower turns 2, is determined in large measure by the size of the vessel into which the stent 20 will be implanted. Additionally, each stent segment 10 may define N number of turns, N being preferable between 2 and 10. In the stent segments 10 shown in the drawings, the segments define four upper and four lower axial turns 2. The stent segments 10 may be connected together by articulated or rigid joints, or they may be deployed in a multiple spaced apart, non-connected configuration. The implanted encapsulated stent assembly 20 will preferably be of sufficient length as to maintain its axial orientation with the vessel without shifting under the hydraulics of blood flow (or other fluid flow in different types of vessels), while also being long enough to extend across at least a significant portion of the affected area. At the same time, the encapsulated stent 20 should be short enough as to not introduce unnecessarily large amounts of material as might cause undue thrombosis.

Figure 2:
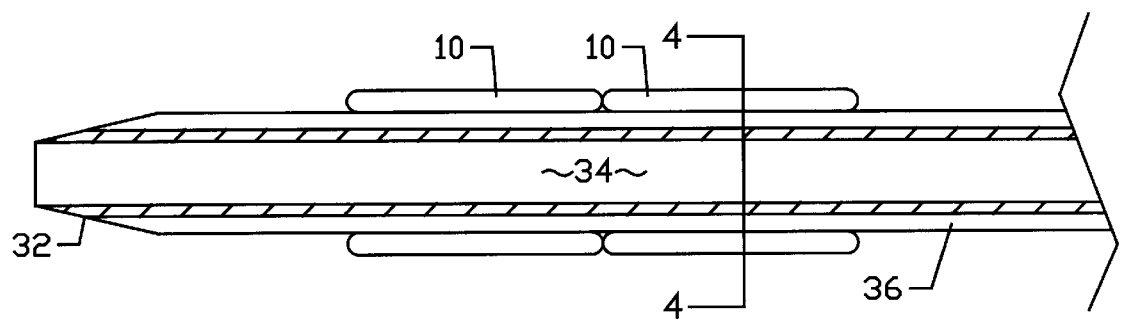
FIG. 2 is a longitudinal cross sectional view of the stents of FIG. 1 compressed upon a balloon of a balloon catheter and shown prior to the encapsulation process.

Following selection of the configuration and size of a stent segment 10, or multiple connected or non-connected stent segments, the segment or segments 10 are compressed upon the outside of the balloon 36 of the balloon catheter 30 as best shown in FIGS. 2 and 4. An interior sheath 42 is placed over each end of the balloon catheter 30, and an exterior sheath 44 is placed over the interior sheath 42 to cover the stent segments 10 and overlap with the interior sheath 42. The sheaths 42, 44 are preferably non-expandable, and of a size to accept insertion of the stent segments 10 mounted on the balloon. Sheaths 42, 44 are shown for example only, and it will be recognized by those skilled in the art that the balloon catheter and stents compressed thereon also may be placed within a mold to prevent expansion of the stent and configured to allow expansion of the balloon as desired.

Next, the balloon catheter 30 preferably is pressurized by introducing air, or an inert gas such as nitrogen, through the lumen 34 into the interior of the balloon to partially expand the balloon 36 within the sheaths 42, 44. The assembly then is exposed to an elevated temperature while maintaining pressurization of the balloon. The pressure may be, for example, approximately 70 psi, and the elevated temperature may be achieved by placing the sheathed assembly into an oven at approximately 150 degrees Fahrenheit to accomplish the heating step.

Figure 5:
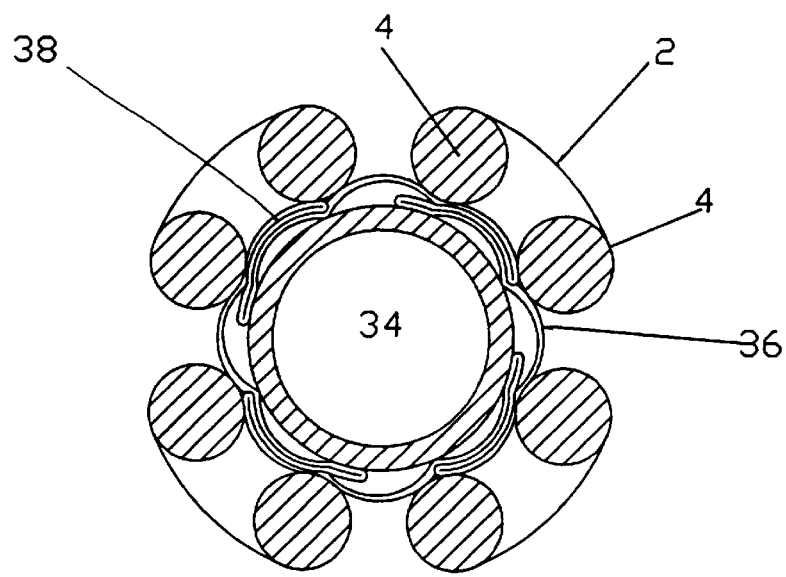
FIG. 5 is a cross sectional view showing the partially inflated form of the balloon around the stent.
Figure 6:
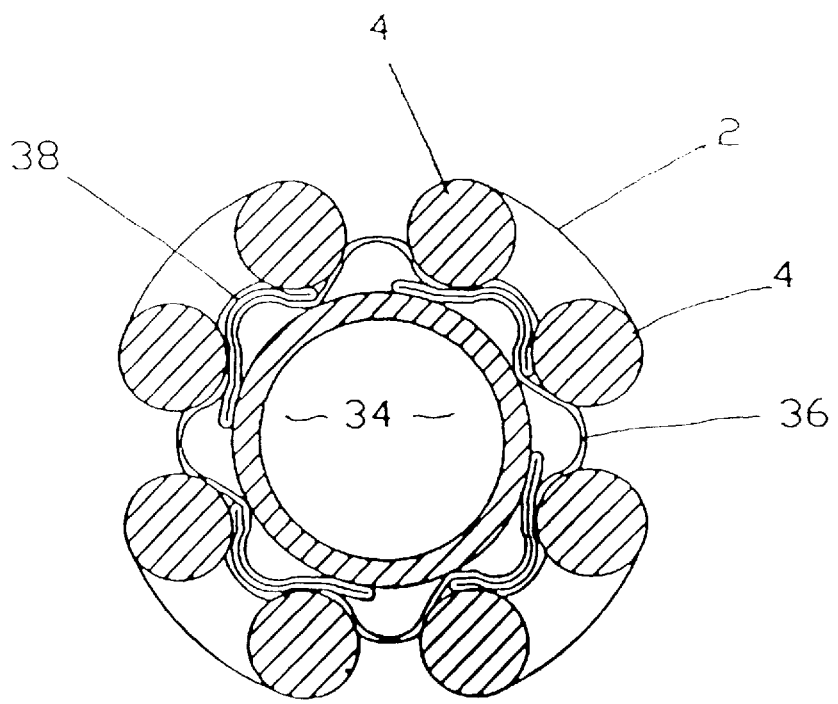
FIG. 6 is a cross sectional view taken along lines 6—6 of FIG. 1 and showing the frozen-in form of the balloon around the stent.

FIGS. 4–6 demonstrate, respectively, the configuration of the balloon 36 prior to pressurization, the configuration during inflation, and the frozen-in form configuration around and adhering to a stent segment 10. The balloon 36, and the wings 38, expand partially outwardly to occupy spaces around the axial turns 2 and between the straight sections 4 so that the balloon 36 and the stent segments 10 are in intimate contact. Those skilled in the art will recognize that expansion of the balloon also depends upon the form of the particular stent selected for encapsulation. Pressure between the stent and the balloon during heating and balloon pressurization causes an adherence upon cooling. Adherence is required for encapsulation which includes both intimate contact between the stent and the balloon as well as contact where the balloon surrounds at least a portion of the stent.

Alternatively, pressurization of the balloon during the heating step is not required where the sheaths 42, 44 fit tightly around the stent-balloon assembly. Pressure radiating inwardly from the sheaths 42, 44 to press against the stents 10 causes the stents 10 to press against the heated balloon to achieve encapsulation.

Following heating, the balloon-stent assembly is removed from the heat and allowed to cool within the sheath. In those cases where the balloon has been pressurized during heating, the internal pressure is maintained. Cooling sets the shape of the balloon 36 which adheres to the stent 10 following cooling, thereby allowing removal of the sheaths 42, 44 for delivery of the assembly 20 within a vessel. Because of the adherence between the stent segment 10 and the balloon 36 of the encapsulated stent assembly 20 and the more regular surface area created by encapsulating stent assembly segments, the encapsulated stent assembly 20 may be delivered without an external sheath.

Figure 3:
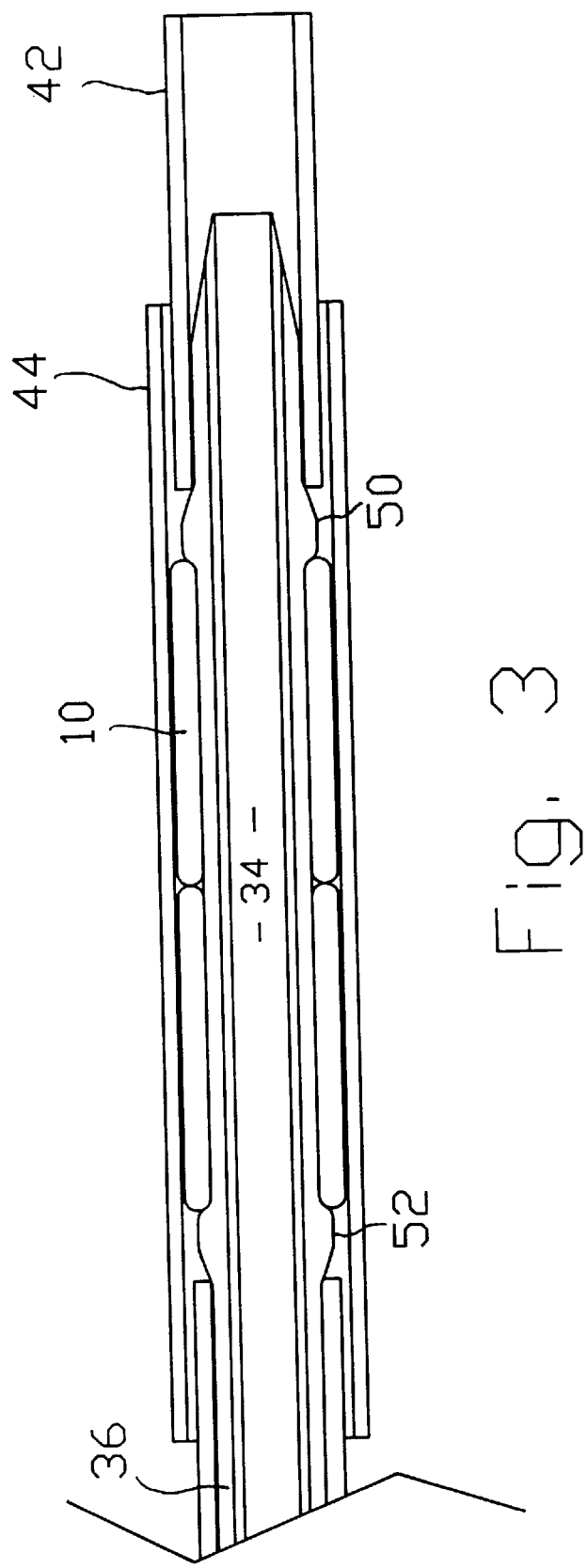
FIG. 3 is a longitudinal cross sectional view of the stents and balloon during the encapsulation process and shown positioned within interior and exterior sheaths.
Figure 7:
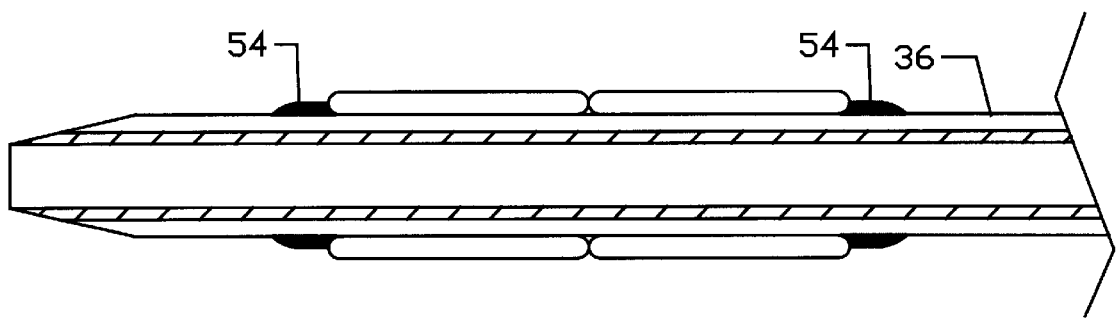
FIG. 7 is a longitudinal cross sectional view of two encapsulated stents and a balloon showing retainers on the outside of the balloon.
Figure 8:
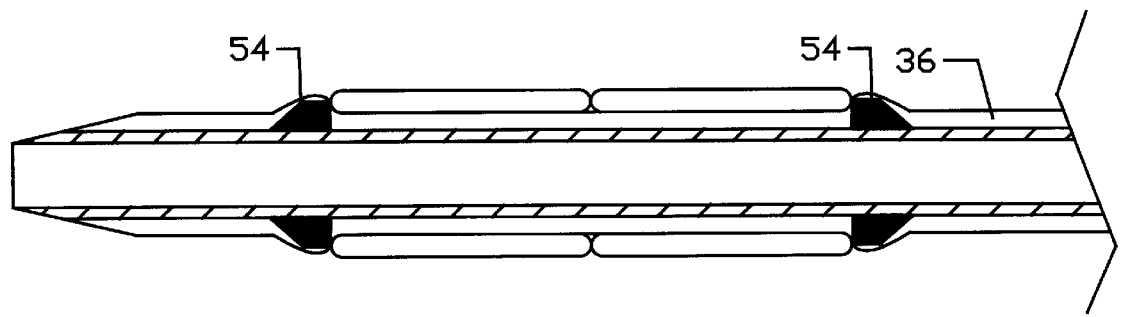
FIG. 8 is a longitudinal cross sectional view of encapsulated stents and a balloon showing retainers on the inside of the balloon and attached to the balloon catheter.

As best shown in FIG. 3, and in FIG. 1, the encapsulated stent assembly 20 may include a distal retainer 50 and/or a proximal retainer 52. The retainers 50, 52 further secure the stent segment 10 to the balloon 36 and create a smooth transition between the balloon/stent area of the delivery device and the distal and proximal surfaces of the delivery device of the encapsulated stent assembly 20. The retainers 50, 52 may be formed by the balloon itself during the encapsulation process, with the configuration of the formed retainers 50, 52 determined by the dimensions of the spaces between the inner sheath 42 and the stent segments 10. Formed retainers 50, 52 may be tapered or non-tapered. Alternatively, conventional retainers 54 may be attached over the balloon 36 prior to encapsulation, as shown in FIG. 7, or the retainers 54 may be placed within the balloon 36, as shown in FIG. 8. One or two retainers 54 may be used, and conventional retainers may be made from any implantable material, such as implantable stainless steel or polymers. Depending upon the configuration of the encapsulated stent assembly 20, retainers generally range in length from 0–20 mm.

The encapsulated stent assembly 20 is delivered to the desired site with or without a guiding catheter and using a conventional guidewire for steerability to negotiate the area to be treated. Conventional radiopaque markers and fluoroscopy may be used with the device for positioning the encapsulated stent assembly and for viewing the expansion procedure. Once the encapsulated stent assembly is in place across the lesion, the balloon may be inflated in a conventional manner. In the embodiment shown in FIGS. 4–6, the four wings 38 expand evenly to form four, symmetrical expanded flutes which symmetrically expand the inner diameter of the encapsulated stent outwardly by increasing the angle at the axial bends. During typical balloon expansion pressures of approximately 6 atmospheres or 90 psi, occurring within the human body and at body temperature, the heat set creases dissipate. The folded and wrapped wing configuration of the balloon ensures that the balloon will provide radially uniform inflation so that the stent will expand substantially equally along each of the peaks. Uniform expansion of the lumen of the vessel occurs with uniform, symmetrical expansion of the encapsulated stent and balloon. The amount of inflation, and commensurate amount of expansion of the stent, may be varied as dictated by the lesion itself, making the stent assembly of the present invention particularly flexible in the treatment of chronic restenosis and abrupt reclosure.

Because of the inflation of the balloon and expansion of the arterial wall of the vessel, the arterial wall bulges radially. At the same time, the plaque deposited within the intima of the vessel is displaced and thinned, and the stent is embedded in the plaque or other fibrotic material adhering to the intima of the vessel.

Following inflation of the balloon and expansion of the encapsulated stent within the vessel, the balloon is deflated so that it pulls away from the stent for removal. The deflated balloon generally forms from 1½ to 2¾ wings, including a generally U-shaped deflated form, and the deflated wings do not retain the creases created by the heat setting balloon formation process discussed above. The deflated balloon easily folds around the balloon catheter for removal.

The exterior wall of the vessel attempts to return to its original shape through elastic recoil. The stent, however, remains in its expanded form within the vessel, and prevents further recoil and restenosis of the vessel. The stent maintains an open passageway through the vessel. Because of the low mass of the preferred support device of the present invention, thrombosis is less likely to occur. Ideally, the displacement of the plaque deposits and the implantation of the stent will result in a relatively smooth inside diameter of the vessel.

While the primary application for the stent is presently believed to be treatment of cardiovascular disease such as atherosclerosis or other forms of coronary narrowing, the stent of the present invention may also be used for treatment of vessels in the kidney, leg, carotid, or elsewhere in the body. In such other vessels, the size of the stent may need to be adjusted to compensate for the differing sizes of the vessel to be treated.

While this invention has been described in connection with preferred embodiments thereof, it is obvious that modifications and changes therein may be made by those skilled in the art to which it pertains without departing from the spirit and scope of the invention. For instance, the encapsulation method and deployment is not limited to any particular expandable stent device. Accordingly, the aspects discussed herein are for illustration only and should not limit the scope of the invention herein which is defined by the claims.

What is claimed is:

1. An endovascular support device for implantation in a vessel within the human body comprising:

at least one compressible stent means mounted on a balloon of a balloon catheter; and wherein said at least one compressible stent means is encapsulated by said balloon of said balloon catheter.

2. The endovascular support device of claim 1 wherein the balloon is adhered to the compressible stent means when encapsulated.

3. The endovascular support device of claim 1 further comprising at least one retainer means for facilitating delivery of the encapsulated stent means for implantation.

4. The endovascular support device of claim 3 wherein the balloon forms the at least one retainer means.

5. The endovascular support device of claim 1 wherein the stent means comprises at least one expandable member bent to form a plurality of substantially straight, non-overlapping sections connected by axial bends.

6. A method for treating narrowing of vessels within humans comprising the steps of:

providing at least one endovascular support device;

mounting the at least one endovascular support device on a balloon of a balloon catheter;

anchoring the at least one endovascular support device to the balloon by encapsulation of the at least one endovascular support device by the balloon;

advancing the balloon catheter and the at least one encapsulated endovascular support device to an area to be treated within the vessels;

inflating the balloon of the balloon catheter to expand the at least one encapsulated endovascular support device within the area to be treated; and deflating the balloon of the balloon catheter so that the balloon pulls away from the at least one endovascular support device.

7. A delivery system for an endovascular support device comprising:

a balloon catheter having a catheter body and a balloon;

means for selectively inflating and deflating said balloon;

at least one endovascular support device mounted on said balloon, said at least one endovascular support device having a first diameter for intraluminal delivery and a second expanded diameter for deployment in a vessel;

wherein said balloon at least partially surrounds at least a portion of said at least one endovascular support device thereby securing said at least one endovascular support device to said balloon for intraluminal delivery.

8. The delivery system according to claim 7 wherein the at least one endovascular support device is retained in indentations formed in said balloon.

9. The delivery system according to claim 7 wherein the balloon adheres to the at least one endovascular support device.

10. The delivery system according to claim 7 further comprising at least one retainer means for facilitating delivery of said at least one endovascular support device to a predetermined location within a vessel.

11. The delivery system according to claim 10 wherein the balloon forms the at least one retainer means.

12. The delivery system according to claim 7 wherein the at least one endovascular support means comprises at least one expandable member in the form of a plurality of substantially straight segments connected by axial bends.

13. The delivery system according to claim 12 wherein said at least one expandable member is mounted onto said balloon to have an interior diameter $D_i$ and wherein portions of said balloon protrude through said substantially straight segments to have a diameter greater than $D_i$.

14. A method for treating narrowing of vessels within humans comprising the steps of:

introducing a stent delivery system into a vessel, the stent delivery system comprising at least one endovascular support device mounted on a balloon of a balloon catheter, the at least one endovasular support device anchored to the balloon by encapsulation of the at least one endovascular support device by the balloon;

advancing the stent delivery system to an area to be treated within the vessels;

inflating the balloon of the balloon catheter to expand the at least one encapsulated endovascular support device within the area to be treated; and deflating the balloon of the balloon catheter so that the balloon pulls away from the at least one endovascular support device.

* * * * *